(12) United States Patent
Yang et al.

(10) Patent No.: US 10,052,233 B2
(45) Date of Patent: Aug. 21, 2018

(54) PROTECTIVE VISOR

(71) Applicant: Ningbo Geostar Photoelectric Technology Co., Ltd, Ningbo (CN)

(72) Inventors: Zhaolin Yang, Ningbo (CN); Jianrong Zhou, Ningbo (CN); Rongjiang Wang, Ningbo (CN)

( * ) Notice: Subject to any disclaimer, the term of this patent is extended or adjusted under 35 U.S.C. 154(b) by 35 days.

(21) Appl. No.: 15/172,583

(22) Filed: Jun. 3, 2016

(65) Prior Publication Data
US 2017/0252214 A1    Sep. 7, 2017

(30) Foreign Application Priority Data

Mar. 1, 2016  (CN) .......................... 2016 1 0115578

(51) Int. Cl.
*A61F 9/02* (2006.01)

(52) U.S. Cl.
CPC .............. *A61F 9/025* (2013.01); *A61F 9/023* (2013.01); *A61F 9/027* (2013.01)

(58) Field of Classification Search
CPC .......... A61F 9/025; A61F 9/023; A61F 9/027; A42B 3/185; A42B 3/28
USPC ................................................ 2/427, 424, 9
See application file for complete search history.

(56) References Cited

U.S. PATENT DOCUMENTS

| | | | | |
|---|---|---|---|---|
| 797,293 A * | 8/1905 | Lang et al. | ............. | G02C 7/16 2/12 |
| 2,410,256 A | 10/1946 | Anderson et al. | | |
| 2,758,307 A * | 8/1956 | Treiber | .................... | A61F 9/025 2/8.1 |
| 3,400,407 A * | 9/1968 | Aileo | ..................... | A42B 3/221 2/427 |
| 3,868,727 A * | 3/1975 | Paschall | .................. | A61F 9/064 2/12 |
| 4,117,553 A * | 10/1978 | Bay | ........................ | A42B 3/225 2/10 |
| 4,170,042 A * | 10/1979 | Aileo | ..................... | A42B 3/228 2/424 |
| 4,852,185 A * | 8/1989 | Olson | ....................... | A61F 9/02 2/9 |
| 4,856,109 A * | 8/1989 | Desy | ...................... | A61F 9/025 2/424 |

(Continued)

FOREIGN PATENT DOCUMENTS

| | | |
|---|---|---|
| CN | 2845786 Y | 12/2006 |
| CN | 101926704 A | 12/2010 |

*Primary Examiner* — Alissa L Hoey

(57) ABSTRACT

The disclosure provides a protective visor applicable to multiple operation environments for dust prevention, anti-shock glasses, chemical defense and ray radiation protection. The protective visor comprises a headband, a face shield, protective goggles, a light shading screen, a light grid and a housing, which are connected to each other. The light shading screen and the light grid constitute a light refraction and transmission device for refracting and transmitting the light, which includes a light aperture processed to have a curved surface and located at the front and upper end portion of the housing. The light aperture has a serrated lattice shutter structure, and the light shading screen is disposed at the outer side of the light aperture. The protective visor can effectively prevent foreign splash, and absorb radiant heat and certain ultraviolet rays to protect an operator's face.

4 Claims, 5 Drawing Sheets

(56) References Cited

U.S. PATENT DOCUMENTS

| | | | | |
|---|---|---|---|---|
| 4,986,282 A * | 1/1991 | Stackhouse | A61F 9/02 128/857 |
| 5,247,706 A * | 9/1993 | Mark | A61F 9/025 2/13 |
| 5,440,760 A * | 8/1995 | Highsmith | A41D 13/11 128/857 |
| 5,647,060 A * | 7/1997 | Lee | A41D 13/11 128/857 |
| 5,673,431 A * | 10/1997 | Batty | A42B 3/225 2/10 |
| 5,966,738 A | 10/1999 | Wang | |
| 6,457,180 B1 | 10/2002 | Jung | |
| 6,606,751 B1 * | 8/2003 | Kalhok | A42B 3/226 2/424 |
| 7,398,560 B1 * | 7/2008 | Swensen | A42B 1/062 2/182.2 |
| 7,716,754 B1 * | 5/2010 | Ross | A42B 3/24 2/410 |
| 7,725,949 B2 * | 6/2010 | Landis | A61F 9/022 2/206 |
| 8,291,512 B2 * | 10/2012 | Stoll | A41D 13/1184 2/15 |
| 8,291,513 B2 * | 10/2012 | Prinkey | A42B 3/22 2/15 |
| 8,336,123 B2 * | 12/2012 | Gleason | A41D 13/1184 2/10 |
| 8,341,771 B2 * | 1/2013 | Lee | A42B 3/226 2/15 |
| 2007/0136933 A1 * | 6/2007 | Kim | A42B 3/226 2/424 |
| 2007/0220649 A1 * | 9/2007 | Huh | A61F 9/025 2/9 |
| 2011/0277224 A1 * | 11/2011 | Okuma | A42B 3/225 2/424 |
| 2012/0084904 A1 | 4/2012 | Paulson | |
| 2015/0351965 A1 * | 12/2015 | Umentum | A61F 9/04 221/92 |

* cited by examiner

PROTECTIVE VISOR

CROSS-REFERENCE TO RELATED APPLICATION(S)

This application claims priority under 35 § 119(a)-(d) to Chinese Patent Application Serial No. 201610115578.0, titled "A Novel Protective Visor," filed Mar. 1, 2016, which is incorporated herein by reference in its entirety.

TECHNICAL FIELD

The present disclosure relates to a face protection apparatus for special operational environment, applicable to a variety of operation environments for dust-prevention, anti-shock glasses, chemical defence, ray radiation protection, etc. Such operation environments include electrical welding, gas welding, steel, punch tool, brush cutter, grinder, iron manufacturing, glass treatment, chemical treatment, garden shredder, blown glass and other operation environments. In particular, the invention relates to a novel protective visor.

BACKGROUND

Conventional protective face screen or visor can be divided into welding protective visor, anti-chemical warfare visor, and anti-shock visor. The protective visor has a head-mounted or hand-held structure. The head-mounted protective visor consists of a headband and a face screen. When an operator works wearing such a protective visor on head, the protective visor can effectively prevent foreign splash, and absorb radiant heat as well as certain ultraviolet (UV) rays. Human face can be protected effectively. However, the conventional protective face screen or visor cannot effectively filter out harmful rays from incidence, and thus leaves operator's eyes subject to injury.

SUMMARY

To solve the above-mentioned problems, the present disclosure provides a novel protective visor, including a headband, a face shield, protective goggles, a light shading screen, a light grid and a housing which has a brim, where these above-mentioned components are connected to each other.

The light shading screen and the light grid constitute a light refraction and transmission device for refracting and transmitting the light. The light refraction and transmission device includes a light aperture that is processed to have a curved surface and located at the front and upper end portion of the housing, where the light aperture has a serrated lattice shutter structure, and the light shading screen is disposed at the outer side of the light aperture.

The protective goggles have an adjustment guide rail on both sides of the protective goggles respectively. The upper end of the protective goggles is connected to the light shading screen and the light grid via an adjustment slider. After assembly, the adjustment slider and the protective goggles locate at fixed relative position. In the middle portion of the light shading screen, a sliding region for the adjustment slider is disposed. When the adjustment slider is sliding up and down the sliding region in the middle of the light shading screen, the protective goggles can be driven to move up and down, and thus the adjustment of the position of the protective goggles can be achieved.

After an operator puts on the protective visor correctly according to the wearing method of the traditional head-mounted visor, the face shield can be adjusted to different angles, and the protective goggles can be moved to different positions according to different needs under different operation environments. When the protective goggles is not needed, they can be placed to the top of the face shield by adjusting the adjustment slider of the light refraction and transmission device. In addition, by placing the protective goggles to the top position, the protective goggles can effectively absorb the light transmitting through the light refraction and transmission device and thus effectively prevent incidence of the glares harmful to human.

The light shading screen is made of dark colored translucent polycarbonate, which is used to effectively shield against harmful glares, ultraviolet (UV) rays and blue rays.

The above-described novel protective visor can be set as desired. For example, the protective visor may not include the protective goggles and their gear device, e.g., the adjustment guide rail and the adjustment slider. The sliding structure may be removed from the light shading screen and the shape of the light shading screen may be changed to a curved model structure with a ventilation hole.

The beneficial effects of the present disclosure include the following.

First, the present disclosure adds a light refraction and transmission device based on the traditional protective face screen or visor. The light refraction and transmission device constructs a specially shaped light transmission area at the front and upper end portion of the housing of the traditional protective visor. The light firstly travels through the transparent layer (the light shading screen) that has a certain light penetrability. The light shading screen effectively shields against some harmful lights such as glares, ultraviolet (UV) rays, blue rays and so on. After going through the light shading screen, the light beats directly onto the light aperture that has a serrated lattice shutter structure, through which the light travels by multiple refractions with different angles to reach the inner side of the face shield. This is designed based on precision optics principles. These irregularly refracted lights are effectively aligned and filtered to be adjusted to light in the same direction to go into the eyes. Therefore the light looks soft without glare, thus reducing glare symptoms of the operator. Furthermore, the passing light provides more adequate light to the operation environment, effectively reducing fatigue in long-time operation and thereby simultaneously protecting the operator's eyes.

Second, the present disclosure adds protective goggles on the traditional protective face screen or visor. The lens of the protective goggles are made of such material as polycarbonate. This material has excellent impact strength properties, a high refractive index, light gravity, and inner permanent anti-fog, anti-oil, waterproof and anti-static properties, and 100% UV protection. The shades of the lens can be chosen based on the strengths of different arc lights in different operations.

Third, the present disclosure connects the light refraction and transmission device with the protective goggles via a gear device. It allows the operator to adjust the adjustment slider of the gear device to place the protection googles to an appropriate position according to different operation environments.

BRIEF DESCRIPTION OF DRAWINGS

Appended drawings will be briefly described in order to illustrate the preferred embodiments of the present disclosure. The brief description of the appended drawings is provided below.

Figure 1:
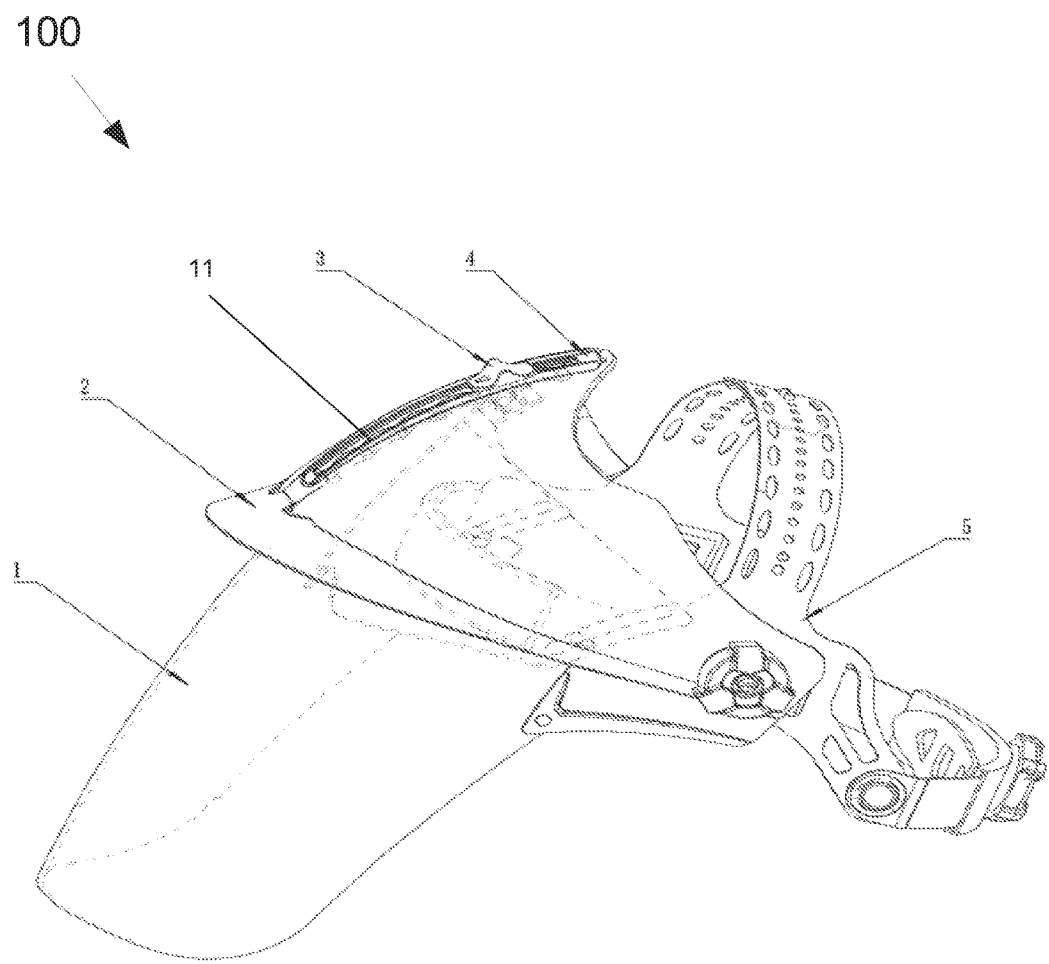
FIG. 1 is a structure diagram of a novel protective visor according to one embodiment of this disclosure.

In the drawings, the reference signs include the following.
1. Face shield, 2. Housing, 3. Adjustment slider, 4. Light shading screen, 5. Headband, 6. Protective goggles, 7. Adjustment clip, 8. Light grid, 9. Adjustment guide rail, 10. Ventilation hole.

DETAILED DESCRIPTION

The exemplary embodiments of the disclosure will be described clearly and completely in combination with the appended drawings in order to clarify the purposes and advantages of the present disclosure. Apparently the to-be-described exemplary embodiments are only part of the embodiments of the disclosure, and not a complete set of the embodiments. Other embodiments obtained by one skilled in the related art based on the embodiments described in this present disclosure without any creative effort will be included within the protection scope of this disclosure.

Referring to FIGS. 1-5, the exemplary embodiments employ the following technical solutions. The embodiments of this disclosure are illustrated below in further detail by referring to Figures.

FIG. 1 is a structure diagram of a novel protective visor 100 according to one embodiment of this disclosure. The novel protective visor 100 includes a headband (5), a face shield (1), protective goggles (6), a light shading screen (4), a light grid (8), an adjustment slider (3), an adjustment guide rail (9) and a housing (2). The housing (2) has a front and upper portion, and side portions. The front and upper portion of the housing has an outside surface and an inner side surface. The headband (5) and the face shield (1) are both connected to the side portions of the housing (2).

Figure 2:
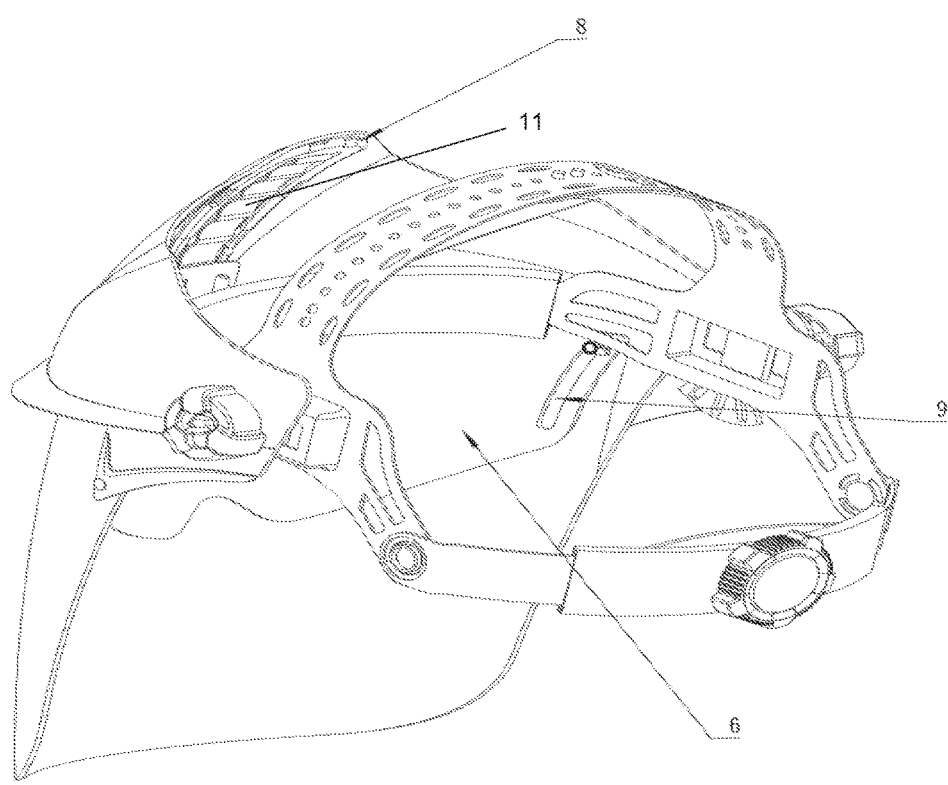
FIG. 2 is a structural diagram of a light refraction and transmission device and protective goggles of the novel protective visor according to one embodiment of the disclosure.

The above-described light refraction and transmission device is a light aperture 11 that is processed to have a special shape, e.g., the serrated lattice shutter structure shown as reference sign (8) in FIG. 2, and located at the front and upper end portion of the housing (2). The light aperture 11 has the light shading screen (4) disposed at the outer side of the light aperture 11. The light shading screen (4) is made of a special material such as polycarbonate, and is dark color and translucent, and thereby effectively shields against harmful glares, ultraviolet (UV) rays, blue rays, etc.

Still referring to FIG. 1, the light shading screen (4) has a sliding region in the middle portion and the adjustment slider (3) is connected to the sliding region and movable up and down the sliding region. The protective goggles (6) is shown as dotted lines in FIG. 1. An upper end of the protective goggles (6) is connected to the light shading screen (4) and the light grid (8) via the adjustment slider (3). After assembly, the adjustment slider (3) and the protective goggles (6) can be fixed to each other. The protective goggles (6) may be driven by the adjustment slider (3) to move up and down so that the position of the protective goggles (6) is adjusted.

FIG. 2 is a structural diagram 200 of a light refraction and transmission device and protective goggles of the novel protective visor 100 according to one embodiment of the disclosure. Referring to FIG. 2, the protective goggles (6) have an adjustment guide rail (9) disposed on both sides of the goggles (6) respectively. The upper end of the protective goggles (6) is connected to the light shading screen (4) and the light grid (8) via an adjustment slider (3). After assembly, the adjustment slider (3) and the protective goggles (6) can be fixed together. In the middle portion of the light shading screen (4), the sliding region for the adjustment slider is set. When the adjustment slider (3) is sliding up and down the sliding region in the middle of the light shading screen, the protective goggles can be driven to move up and down, and thus the adjustment of the position of the protective goggles can be achieved.

After an operator wears the protective visor correctly according to the wearing method of the traditional head-mounted visor, the face shield (1) can be adjusted to an appropriate angle. The protective goggles (6) can be moved up and down to desired positions according to different needs under different operation environments. When the protective goggles is not needed, the protective goggles (6) can be placed to the front and upper end of the housing (2) by adjusting the adjustment slider (3) of the light refraction and transmission device, thus avoiding to affect the operation vision. In addition, by placing the protective goggles (6) to the top position, the protective goggles (6) can effectively absorb the light passing through the light refraction and transmission device and thus effectively prevent the incidence of the UV rays.

Figure 3:
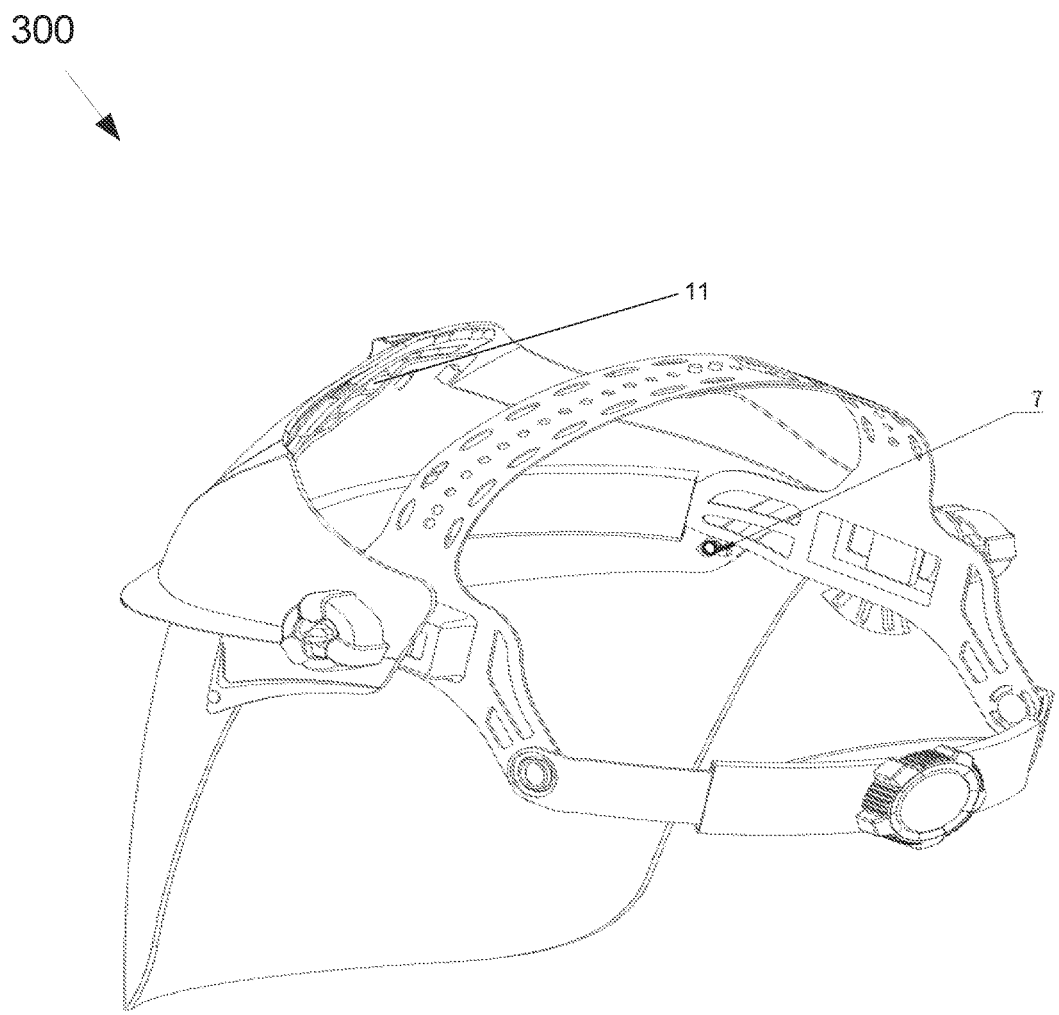
FIG. 3 is a diagram of an adjustment clip of the novel protective visor according to one embodiment of the disclosure.

FIG. 3 is a diagram 300 of an adjustment clip of the novel protective visor according to one embodiment of the disclosure. Referring to FIG. 3, the adjustment clip (7) is placed inside the adjustment guide rail (9) on either or both sides of the protective goggles (6). The adjustment clip (7) is used to fix the relative position of the protective goggles (6). For example, when the adjustment slider (3) slides up and down, the protective goggles (6) is driven to move up and down accordingly, and the adjustment clip (7) changes relative position inside the adjustment guide rail (9). Once a desired position is determined by the operator, the adjustment clip (7) can be used to fasten the protective goggles (6) to the desired position.

The protective goggles (6) and their gear device (e.g., the adjustment guide rail (9), the adjustment slider (3), and the adjustment clip (7)) in the present disclosure can be equipped optionally according to different users' desires. For example, the protective visor can be made without the protective goggles and the gear device by changing the design of the light shading screen.

Figure 4:
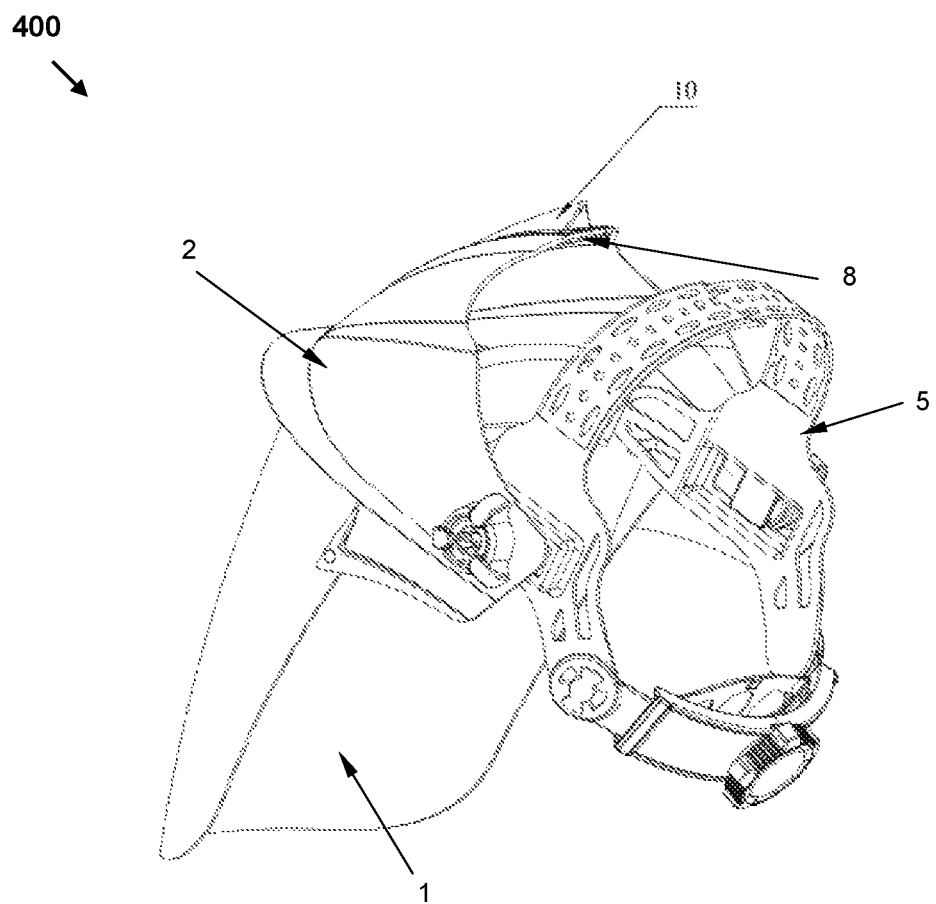
FIG. 4 is a diagram of a face shield of the novel protective visor without the protective goggles and their gear device according to one embodiment of the disclosure.
Figure 5:
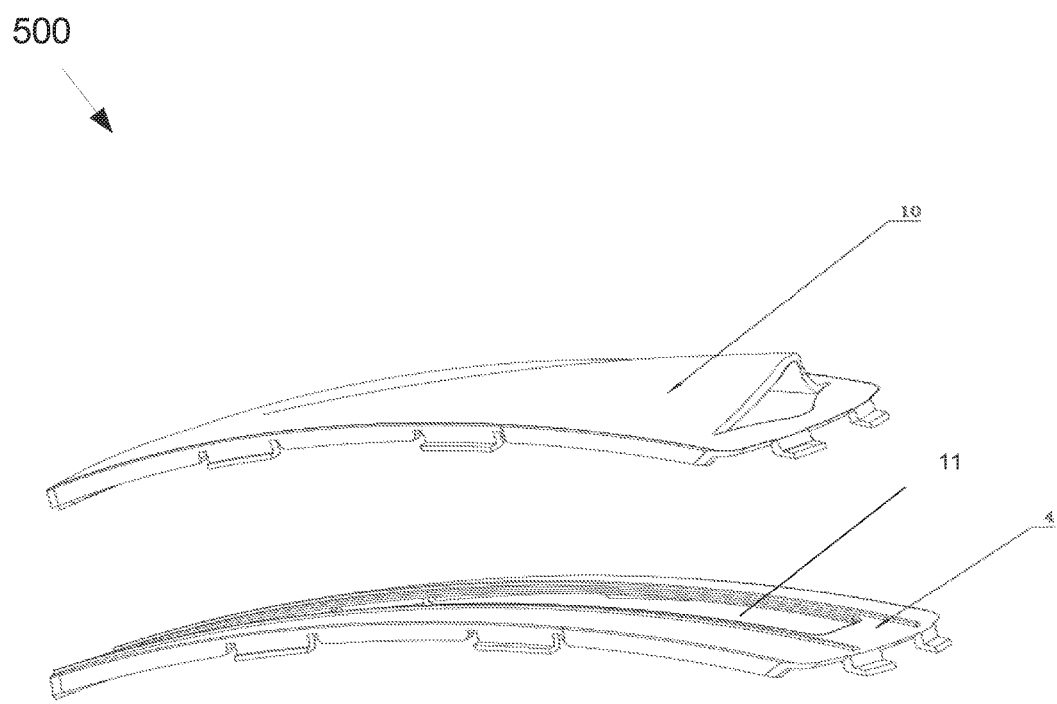
FIG. 5 is a diagram of a ventilation hole of the novel protective visor according to one embodiment of the disclosure.

FIG. 4 is a diagram 400 of a face shield of the novel protective visor without the protective goggles and their gear device according to one embodiment of the disclosure. FIG. 5 is a diagram 500 of a ventilation hole (10) of the novel protective visor according to one embodiment of the disclosure. Referring to FIGS. 4 and 5, the sliding structure may be removed from the light shading screen (4) in FIG. 1 and the light shading screen (4) may be changed to an arch shape, as shown in FIG. 4. For example, the light shading screen (4) may have a top end, and the top end is an arch constructing a ventilation hole (10). Alternatively, the top end has a shape of a tunnel hollowed out in a mountain range, as shown in FIGS. 4 and 5.

What is claimed is:

1. A protective visor, the protective visor comprising:
a headband, a face shield, protective goggles, a light shading screen, a light grid, an adjustment slider and a housing;
wherein the housing has a front and upper portion, and side portions, and wherein the front and upper portion of the housing has an outside surface and an inner side surface;
wherein the headband and the face shield are both connected to the side portions of the housing;
wherein the light shading screen is connected to and located at the outside surface of the front and upper portion of the housing, and wherein the light grid is connected to and located at the inner side surface of the front and upper portion of the housing, and wherein between the light shading screen and the light grid a light aperture is formed and disposed on a curved surface of the face shield, and is located above the front and upper portion of the housing and wherein the light shading screen has a sliding region that is for disposing the adjustment slider and is in a middle portion of the light shading screen and
wherein the adjustment slider is connected to the sliding region and movable up and down the sliding region,
wherein an upper end of the protective goggles is connected to the light shading screen and the light grid via the adjustment slider,
wherein the adjustment slider and the protective goggles are fixed to each other, and
wherein the protective goggles are driven by the adjustment slider to move up and down so that the position of the protective goggles is adjusted.

2. The protective visor of claim 1, wherein the light shading screen is made of dark colored translucent polycarbonate.

3. The protective visor of claim 1, wherein the protective goggles are adjustable to the front and upper portion of the housing by adjusting the adjustment slider.

4. The protective visor of claim 1 further comprises an adjustment guide rail and an adjustment clip, wherein the adjustment guide rail is located on one side portion of the protective goggles, and wherein the adjustment clip is connected to the side portion of the housing and is placed inside the adjustment guide rail.

* * * * *